United States Patent
Libin et al.

(10) Patent No.: US 10,744,099 B2
(45) Date of Patent: *Aug. 18, 2020

(54) RADIATION STERILIZATION OF HYPERCOMPRESED POLYMER DOSAGE FORMS

(71) Applicant: Sustained Nano Systems LLC, Westhampton Beach, NY (US)

(72) Inventors: Barry M. Libin, Westhampton Beach, NY (US); Jeffrey M. Liebmann, Great Neck, NY (US); Weiliam Chen, Mt. Sinai, NY (US)

(73) Assignee: SUSTAINED NANO SYSTEMS LLC, Westhampton Beach, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/688,881

(22) Filed: Nov. 19, 2019

(65) Prior Publication Data

US 2020/0085755 A1 Mar. 19, 2020

Related U.S. Application Data

(63) Continuation of application No. 16/031,665, filed on Jul. 10, 2018, now Pat. No. 10,500,163.

(60) Provisional application No. 62/531,239, filed on Jul. 11, 2017.

(51) Int. Cl.
| | | |
|---|---|---|
| *A61K 9/50* | (2006.01) | |
| *A61K 47/34* | (2017.01) | |
| *A61L 2/08* | (2006.01) | |
| *A61K 9/00* | (2006.01) | |
| *A61K 9/20* | (2006.01) | |
| *A61L 2/00* | (2006.01) | |
| *A61K 31/573* | (2006.01) | |
| *A61K 9/16* | (2006.01) | |

(52) U.S. Cl.
CPC .......... *A61K 9/5089* (2013.01); *A61K 9/0024* (2013.01); *A61K 9/1647* (2013.01); *A61K 9/204* (2013.01); *A61K 31/573* (2013.01); *A61K 47/34* (2013.01); *A61L 2/007* (2013.01); *A61L 2/087* (2013.01)

(58) Field of Classification Search
None
See application file for complete search history.

(56) References Cited

U.S. PATENT DOCUMENTS 10,406,102 B2 * 9/2019 Libin .................... A61K 9/5031
10,500,163 B2 * 12/2019 Libin .................... A61K 9/0024

* cited by examiner

*Primary Examiner* — Jeffrey T. Palenik
(74) *Attorney, Agent, or Firm* — Hedman & Costigan, P.C.; James V. Costigan; Kathleen A. Costigan

(57) ABSTRACT

A sterile pharmaceutical dosage form which comprises an ester capped lactide polymer, glycolide polymer or a lactide-glycolide copolymer hypercompressed with an active pharmaceutical ingredient wherein said sterile pharmaceutical dosage form has been sterilized with an electron beam and a method of preparing said sterile pharmaceutical dosage form.

18 Claims, No Drawings

RADIATION STERILIZATION OF HYPERCOMPRESED POLYMER DOSAGE FORMS

This application is a continuation of Ser. No. 16/031,665, filed Jul. 10, 2018 and provisional application Ser. No. 62/531,239, filed Jul. 11, 2017.

FIELD OF THE INVENTION

This invention relates to the field of sterilization of active pharmaceutical ingredients (API) dispersed in biologically compatible polymeric materials that have been hypercompressed (densified) to form controlled release pharmaceutical formulations.

BACKGROUND OF THE INVENTION

Hypercompressed (densified) biologically compatible lactide polymer, glycolactide or lactide-glycolactide copolymers containing APIs are known. For many applications of these products, it is desirable to utilize radiation to sterilize these products prior to administration to or implantation in a patient. However, these hypercompressed polymers or copolymers are susceptible to degradation when sterilized with radiation. When the API is a thermally unstable material such as a polypeptide or a protein, it is essential to use radiation for sterilization because those solid formulations may only be sterilized by radiation as production of these products in a sterile by process method is not practicable. The applicant has observed that when gamma radiation is applied to make a sterile product based on a polymeric material comprising a lactide polymer, glycolactide or lactide-glycolactide copolymer, these polymeric materials and any polypeptide or protein, which is present, may be degraded or denatured. This can result in a product where the API fails to meet regulatory standards for potency.

It is known that ionizing radiation interacts with the electrons of polymer molecules with a transfer of energy that results in ion formation and ejection of secondary electrons. Depending on the level of kinetic energy of the secondary electrons, there can be further ionization and excitation of other molecules present in the vicinity. The immediate outcome of the exposure to ionizing radiation, such as gamma radiation, is the formation of various energetic species such as trapped radicals, electrons and ions; the decays of these energetic species results in fragmentation and generates free radicals. Such events can both destabilize (chain scission) and stabilize (crosslinking) the polymeric material and or the API.

A significant factor affecting the interaction between the reactive species of degraded peptides and proteins is their proximity to each other. Since hypercompression positions reactive species in closer proximity to one another, the hypercompression actually can facilitate further degradation which results in a reduction in the potency of the product as well as a less stable product with a shorter shelf life.

Current pharmaceutical regulations exist in the United States and in Europe that limit the amount of substances in pharmaceuticals which are related to the active pharmaceutical ingredient to no more than 1.0 wt % or 5 µg TDI (total daily intake) whichever is lower. for a maximum daily dose of 1.0 mg. These related substances have been detected in radiation sterilized polymer or copolymer containing pharmaceuticals at levels that make the products unusable for therapeutic purposes.

It has been found that when a hypercompressed dexamethasone/PLGA product is sterilized by gamma-irradiation, the results show that the level of radiation induced degradation byproducts are relatively high (2.35% when acid terminated PLGA was used and 2.16% when ester-capped PLGA was used). When electron beam irradiation for sterilization is used with ester capped PLGA, the radiation induced degradation byproduct was substantially reduced (between 0.89% to 1.03%).

The present invention is based on the discovery that the use of an electron beam sterilization technique avoids the degradation problems that arise with gamma radiation sterilization of hypercompressed pharmaceutical controlled release products made with ester capped lactide polymers, ester capped glycolactide polymers or ester capped lactide-glycolactide copolymers.

SUMMARY OF THE INVENTION

The present invention provides a sterile pharmaceutical dosage form which comprises an ester capped lactide polymer, an ester capped glycolide polymer or an ester capped lactide-glycolide copolymer hypercompressed with an active pharmaceutical ingredient wherein said sterile pharmaceutical dosage form has been sterilized with an electron beam.

The present invention also includes a method of preparing a sterile hypercompressed pharmaceutical dosage form of an ester capped lactide polymer, an ester capped glycolide polymer or an ester capped lactide-glycolide copolymer which comprises:

(a) combining an active pharmaceutical ingredient with an ester capped lactide polymer, an ester capped glycolide polymer or an ester capped lactide-glycolide copolymer to form a powdered product;

(b) compressing the powdered product of step (a) to form a hypercompressed dosage form; and (c) exposing the hypercompressed dosage form of step (b) to a sterilizing amount of an E-beam radiation source to form a sterilized product.

The method of the invention allows for the use of room temperature during sterilization of a polypeptide or protein API in a hypercompressed controlled release ester capped lactide polymer, ester capped glycolide polymer or ester capped lactide-glycolide copolymer pharmaceutical formulation by the use of electron beam sterilization.

Accordingly, it is an object of the invention to provide novel sterile pharmaceutical formulations which comprise a polypeptide or protein API in a sterile hypercompressed controlled release ester capped lactide polymer or ester capped glycolide polymer or ester capped lactide-glycolide copolymer pharmaceutical formulations.

It is also an object of the invention to provide a method for the sterilization of a polymeric material comprising an ester capped lactide polymer, an ester capped glycolactide or an ester capped lactide-glycolactide copolymer and/or a polypeptide or protein API in a hypercompressed controlled release lactide polymer or glycolide polymer or a lactide-glycolactide copolymer pharmaceutical formulation.

It is a further object of the invention to provide a method of administering a sterile ophthalmic therapeutic agent which comprises a polypeptide or protein API in a hypercompressed ophthalmic insert of an ester capped lactide polymer, an ester capped glycolactide polymer or an ester capped lactide-glycolactide copolymer where the ophthalmic therapeutic agent is in the form of microparticles or nanoparticles.

DETAILED DESCRIPTION OF THE INVENTION

Biodegradable polymers, such as poly(L-lactide) (PLLA) and poly(lactide-co-glycolide) (PLGA), have been utilized in biomedical and pharmaceutical applications. They have been formulated as nanoparticles, microparticles, injectable depots, films, scaffolds, and as a bulk implant for drug delivery, due to their excellent toxicological profile and tunable biodegradability. These controlled drug delivery systems are gaining practical importance because they improve treatment and patient compliance, provide optimized drug concentration on site over prolong periods, and reduce undesired side effects of the drug.

Drug delivery devices formulated from PLGA and PLA and other polymers have been studied for treating diseases of the eye as well as other areas, their hydrolytic degradation, drug release profiles, and mechanical integrity are optimized to suit various applications.

The present invention utilizes an ester capped lactide polymer, an ester capped glycolide polymer or an ester capped lactide-glycolactide copolymer.

PLGA synthesis can be performed by: (i) a direct polycondensation between lactic acid and glycolic acid monomers leading to a copolymer of lower molecular weight,[1,2] or (ii) an opening polymerization of cyclic dimers of lactic acid and glycolic acid leading to a copolymer of higher molecular weight.[3,4,5,6] The typical reaction condition of this type of bulk polymerization is at a temperature in the range of 175° C. in the presence of an initiator such as lauryl alcohol for 2 to 6 hours. Ester-capped PLGA is more stable than acid-capped PLGA as shown by their greater resistant to degradation.[8,9]

The ester capped polymers may be prepared by esterification or transesterification of PLA (polylactic acid), PGY (polyglycolic acid), PGLA polymers or copolymers using polycaprolactone. The ester capped polymers are commercially available or they may be prepared according to well know procedures. Gamma and electron-beam irradiation are among the most popular and well established processes for sterilizing polymer based medical devices. It has been long known, however, that these techniques can lead to significant alterations in the materials being treated. High-energy radiation produces ionization and free radicals in polymer molecules. These energy-rich species undergo dissociation, abstraction, and addition reactions in sequence leading to chemical instability. The destabilization process, which can occur during, immediately after, or even days, weeks, or months after irradiation, often results in physical and chemical cross-linking or chain scission. Resultant physical changes include embrittlement, discoloration, odor generation, stiffening, softening, enhancement or reduction of chemical resistance, and an increase or decrease in melt temperature.

Gamma irradiation causes the radiolytic degradation of an API which comprise a polypeptide or a protein. This produces changes in the biological properties of these materials by modification or destruction of the molecular configuration of the peptide or protein. The extent to which the materials are affected depends on the surface dose delivered. By control of the electron beam energy, the penetration depth of the beam in the hypercompressed dosage form can be manipulated; lower energies produce a shallower penetration depth and therefore avoid modification or destruction of the molecular configuration of the peptide or protein.

Electron beam (E-beam) processing or electron involves using high energy electrons to treat an object for a variety of purposes. This may take place under elevated temperatures and nitrogen atmosphere. Uses for E-beam processing includes sterilization and to cross-link polymers.

The principle of electron beam technology is similar to that of a television set cathode ray tube. The E-beam accelerator creates a beam of electrons approximately 4 inches in diameter and energizes it to near light speed. The beam passes through a scan chamber where a powerful electro-magnetic system scans it back and forth at 200 Hz, creating a curtain of electrons about 4 feet high. A high-speed conveyor carries totes or loaded cartons containing products to be sterilized by the E-beam, where an accurate predetermined dose of radiation is delivered to the product.

Electron energies typically vary from the keV to MeV range, depending on the depth of penetration required. The irradiation dose is usually measured in KiloGray (kGy). NUTEK Corporation has a DualBeam configuration system (see below) whereby product is exposed to two E-beam (10 MeV, 8 KW) accelerators on opposing sides of conveyors as the samples travel through E-beam bunker on a Tote carrier.

The basic components of a typical electron beam processing device are: An electron gun (consisting of a cathode, grid, and anode) is used to generate and accelerate the primary beam. A magnetic optical (focusing and deflection) system is used for controlling the way in which the electron beam impinges on the material being processed (the "workpiece"). In operation, the gun cathode is the source of thermally-emitted electrons that are both accelerated and shaped into a collimated beam by the electrostatic field geometry established by the gun electrode (grid and anode) configuration used. The electron beam then emerges from the gun assembly through an exit hole in the ground-plane anode with an energy equal to the value of the negative high voltage (gun operating voltage) being applied to the cathode. This use of a direct high voltage to produce a high energy electron beam allows the conversion of input ac power to beam power at greater than 95% efficiency, making electron beam material processing a highly energy-efficient technique. After exiting the gun, the beam passes through an electromagnetic lens and deflection coil system. The lens is used for producing either a focused or defocused beam spot on the workpiece, while the deflection coil is used to either position the beam spot on a stationary location or provide some form of oscillatory motion.

Electron beam processing involves irradiation (treatment) of products using a high-energy electron beam accelerator. Electron beam accelerators utilize an on-off technology, with a common design being similar to that of a cathode ray television.

It has been unexpectedly found that electron beam radiation can be utilized to sterilize hypercompressed pharmaceutical compositions without degrading ester capped lactide polymers, ester capped glycolactide polymers or ester capped lactide-glycolactide copolymers to the extent that such polymers will become unusable in pharmaceutical formulations due to the generation of an unacceptable level of degradation products.

However, one factor working against a constant rate of drug release from PLGA and PLLA is that they undergo bulk degradation. The bulk degradation of these polymers is not a predictable phenomenon.

The hypercompressed devices of the invention may comprise an ester capped lactide polymer, an ester capped glycolide polymer or an ester capped lactide-glycolide copolymer that is combined with an API and hypercompressed to form a controlled release dispensing unit. The API that may be mixed with the polymer may comprise hydrophilic or preferably, hydrophobic drugs that are antifungal, antibacterial, antibiotic, anti-inflammatory, immunosuppressive, tissue growth factors, dentinal desensitizers, antioxidants, nutritional agents, vitamins, odor masking agents for example. Specific examples include steroids, non-steroidal anti-inflammatory drugs, antihistamines, antibiotics, mydriatics, beta-adrenergic antagonists, anesthetics, alpha-2-beta adrenergic agonists, mast cell stabilizers, prostaglandin analogues, sympathomimetics, parasympathomimetics, antiproliferative agents, agents to reduce angiogenesis and neovascularization, vasoconstrictors and combinations thereof and any other agents designed to treat disease such as an anti-neoplastic agents such as bevacizumab, ranibizumab, polynucleotide, or peptides or proteins including recombinant protein analogs, an angiogenic inhibitor such as Endostatin, or thalidomide; 5-fluorouracil, paclitaxel, minocycline, timolol hemihydrate, rhHGH, bleomycin, ganciclovir, huperzine, tamoxifen, piroxicam, levonorgesterel, cyclosporin and the like.

Other agents include but are not limited to particular steroids but include steroids such as prednisone, methylprednisolone, dexamethasone; antibiotics including neomycin, tobramycin, aminoglycosides, fluoroquinolones, polymyxin, sulfacetamide, agents such as pilocarpine, isopilocarpine, physostigmine, demecarium, ecothiphate and acetyl choline and salts thereof; mydriatics and cycloplegics including agents such as atropine, phenylephrine, hydroxyamphetamine, cyclopentolate, homatropine, scopolamine, tropicamide and salts thereof; anesthetics include, lidocaine, proparacaine, tetracaine, phenacaine, and the like; beta-blockers such as timolol, carteolol, betaxolol, nadolol, levobunolol, carbonic anhydrase inhibitors such as dorzolamide, acetozolamide, prostaglandin analogues such as latanoprost, unoprostone, bimatoprost or travoprost; recombinant proteins including: Factor VIII, insulin, erythropoetin, vascular endothelial growth factor, fibroblast growth factor, lucocerebrosidase; antibodies for therapy including: abciximab, bevacizumab, pritumumab, ocrelizumab, infliximab and sarilumab; immunotoxins including: denileukin difititox, moxetumomab pasudotox, LMB-2, oportuzumab monatox, HuM195-gelonin, A-dmDT390 and bisFv(UCHT1); cytokines including granulocyte colony stimulating factor, interferon, tumor necrosis factor, interleukin and transformation growth factor-beta: ECM proteins including: elastin, collagen, fibronectin and pikachurin.

Generally a peptide or protein will have a weight average molecular weight of from about 5,000 to 250,000.

Prior to hypercompression, a lactide polymer, a glycolide polymer or a lactide-glycolactide polymer or copolymer and an active pharmaceutical may be formed into microparticles known as microspheres or microcapsules which are typically in the size range of about 2 microns to about 50 microns, preferably from about 2 to about 25 microns and more preferably from about 5 to about 20 microns in diameter. The term microsphere is used to describe a substantially homogeneous structure that is obtained by mixing an active drug with suitable solvents and polymers so that the finished product comprises a drug dispersed evenly in a polymer matrix which is shaped as a microsphere. Depending on the selected size range of the microparticles the term nanoparticle is used to describe structures sized from 1 to 1000 nanometers. A nanometer (nm) is one billionth of a meter or about the size of 10 hydrogen atoms. Currently, nanoparticle drug carriers, i.e. the polymeric material mainly consist of solid biodegradable particles ranging from 50-500 nm in size. Generally a particle size should be selected so that the particles may be easily measured and transferred as necessary for the purpose of placing the particle in a suitable press for the application of hyper-compressive forces to form the compressed dosage form.

Nanoparticles may be formed, for example, by sonicating a solution of polylactide polymer in chloroform containing a 2% w/w solution of polyvinyl alcohol in the presence of a therapeutic agent such as an ophthalmic therapeutic agent for up to 10 minutes, using an ultasonicator (Misonix XL-2020 at 50-55 W power output. Thereafter, the emulsion is stirred overnight at 4° C. to evaporate the chloroform and obtain nanoparticles of the polymer and the therapeutic agent. The medicated nanoparticles can easily access the interior of a living cell and afford the unusual opportunity of enhancing local drug therapy.

Microcapsules may also be used to form the compressed dosage forms of the invention. The term microcapsule is used to describe a dosage form, which is preferably non-spherical and has a polymer shell disposed around a core that contains the active drug and any added excipient which is in the size range set forth above. Generally microcapsules may be made by using one of the following techniques:

(1) phase separation methods including aqueous and organic phase separation processes, melt dispersion and spray drying;

(2) interfacial reactions including interfacial polymerization, in situ polymerization and chemical vapor depositions;

(3) physical methods, including fluidized bed spray coating; electrostatic coating and physical vapor deposition; and (4) solvent evaporation methods or using emulsions with an anti-solvent.

In general, the microparticles are comprised of from about 0.00001 to about 50 parts by weight of therapeutic agent and is further comprised of from about 50 to about 99.9 parts by weight of polymer per 100 parts by weight of the total weight of therapeutic agent and polymer. The preferred ranges are from 1 to 50, 5 to 40, and 20 to 30 parts by weight of therapeutic agent, the balance comprised of polymer. If desired, from 1 to 5 wt % of a binder, such as polyvinyl pyrrolidone, may be homogeneously mixed with the microparticles prior to the compression step.

The amount of drug that is present in an implanted hypercompressed dosage form may vary but generally from 0.5-20% of the usual oral or intravenous dose of the drug may be employed but may vary substantially depending on the solubility, the area of implantation, the patient and the condition to be treated. Microspheres may be formed by a typical in-emulsion-solvent-evaporation technique as described herein.

In order to provide a biodegradable polymeric matrix for a controlled release dosage form which is suitable for placement in a position where a therapeutic agent may be released for treatment of a pathology, the polymer may be selected from ester capped poly(l-lactide), poly(dl-lactide), polyglycolide, poly(glycolide-co-lactide), poly(glycolide-co-dl-lactide), a block polymer of polyglycolide, trimethylene carbonate and polyethylene oxide, or a mixture of any of the foregoing. The synthetic polymer may be a polylactide or a poly(lactide-co-glycolide) with any MW (weight average) or MW polydispersity, all ratios between lactic acid (LA) and glycolic acid (GA), and all degrees of crystallinity. Generally, the MW ranges from about 500 to about 10,000,000 Da, preferably from about 2,000 to about 1,000,000 Da, and more preferably from about 500 to about 5,000 Da. The p(LGA) with the ratio of LA:GA at about 75:25 to about 85:15 (mol:mol) and the MW from about 5,000 to about 500,000 may be used. The lactide/glycolide polymers are bulk-eroding polymers (not surface eroding polymers) and the polymer will hydrolyze when formed into a microparticle matrix as water enters the matrix and the polymer decreases in molecular weight. It is possible to shift the resorption curves to longer times by increasing the polymer molecular weight, using L-polymers and decreasing the surface area by increasing the size of the microparticles or the size of the dosage form. The lactide/glycolide copolymers are available with inherent viscosities as high as 6.5 dl/g and as low as 0.15 dl/g. The lower molecular weight copolymers are preferred for the present invention. It has been found that a mol ratio of 50:50 of glycolide to lactide results in the most rapid degradation and the corresponding release of drug. By increasing the ratio of lactide in the polymer backbone from about 50 mole % to 100% the rate of release can be reduced to provide an extended therapeutic effect from a single dosage unit.

A preferred encapsulating polymer is poly(glycolide-co-dl-lactide) capped with an ester that may be formed with a straight or branched chain aliphatic alcohol or by other means. The ester capped polymeric material which serves as a preferred controlled release delivery system for the dispensing device is similar in structure to the absorbable polyglycolic acid and polyglycolic/polylactic acid suture materials. The polymeric carrier serves as a sustained-release delivery system for the therapeutic agents. The polymers undergo biodegradation through a process whereby their ester bonds are hydrolyzed to form normal metabolic compounds, lactic acid and glycolic acid and allow for release of the therapeutic agent.

Copolymers consisting of various ratios of lactic and glycolic acids have been studied for differences in rates of degradation. It is known that the biodegradation rate depends on the ratio of lactic acid to glycolic acid in the copolymer, and the 50:50 copolymer degrades most rapidly. The selection of a biodegradable polymer system avoids the necessity of removing an exhausted non-biodegradable structure from the eye with the accompanying trauma.

The ester capping of the lactic and glycolic polymers or lactide-glycolide copolymers does not substantially affect the release rates of drugs formulated in these copolymers as compared with lactic acid and glycolic acid copolymers that are not ester capped.

After the microspheres are prepared, they are compressed at very high forces to form the dispensing device of the invention. The hyper-compression may be carried out in an apparatus that is capable or permits the application of from 50,000 to 350,000 psi (hereafter K is used in place of 1,000) pressure to microparticles or nanoparticles, or from 100 Kpsi to 300 Kpsi or 200 Kpsi to 300 Kpsi or 50 or 60 Kpsi to 160 or 170 Kpsi or especially 60 Kpsi to 170 Kpsi The term psi (pounds per square inch) is determined by taking the force in pounds that is applied to the particular dosage form and measuring or calculating the area of the top of the dosage form or die in square inches so that a conversion may be made to express the pressure applied to the dosage form in psi.

The hyper-compressed dispensing device may be a perfect spheroid, but preferably a distorted spheroid such as a flat disc, rod, pellet with rounded or smooth edges that is small enough to be placed under the skin in a location such as bones and their joints, including the knuckles, toes, knees, hips and shoulders; glands, e.g. pituitary, thyroid, prostate, ovary or pancreas, or organs, e.g. liver, brain, heart, and kidney. More particularly, the dispensing device of the invention may be utilized to treat pathology by implanting the device at or near the site of the pathology, or in a way that will affect the pathology, such as any part that comprises the body of a human or animal or fish or other living species. Such parts may include the contents of a cell, any part of the head, neck, back, thorax, abdomen, perineum, upper or lower extremities. Any part of the osteology including but not limited to the vertebral column, the skull, the thorax, including the sternum or ribs, the facial bones, the bones of the upper extremity, such as the clavicle, scapula or humerus; the bones of the hand, such as the carpus; the bones of the lower extremity, such as the ilium or the femur; the foot, such as the tarsus; joints or ligaments; muscles and fasciae; the cardiovascular system, such as the heart, the arteries, the veins, or the capillaries or blood; the lymphatic system, such as the thoracic duct, thymus or spleen; the central or peripheral nervous system, the sensory organs, such as eye, ear, nose; the skin; the respiratory system, such as the lungs, the larynx, the trachea and bronchi; the digestive system, such as the esophagus, the stomach or the liver; the urogenital system, such as the urinary bladder, the prostate, or the ovary; the endocrine glands, such as the thyroid, the parathyroid or the adrenals.

A recombinant humanized monoclonal IgG1 antibody that binds to and inhibits the biologic activity of human vascular endothelial growth factor (VEGF) and is a recognized agent for the treatment of age related macular degeneration (AMD). Bevacizumab contains human framework regions and the complementarity-determining regions of a murine antibody that binds to VEGF. Bevacizumab is produced in a Chinese Hamster Ovary mammalian cell expression system in a nutrient medium containing the antibiotic gentamicin and has a molecular weight of approximately 149 kilodaltons.

EXAMPLE 1

A preparation of hypercompressed PLGA/Dexamethasone particles prepared from an acid terminated PLGA (Purasorb PDLG5002 having an inherent viscosity of 0.16-0.24 dl/g. in chloroform at 25° C., 1.0 g/dl and a 50:50 wt. ratio of lactide to glycolide) by dissolving the PLGA in methylene chloride to make a PLGA/MeCl$_2$ solution a total of 5 ml with 0.23 wt % of dexamethasone. The solvent was evaporated and 250.12 mg of the particles were compressed in a 7.87 mm diameter die using a pressure of 200 Kpsi to form a pellet weighing 242.14 mg having a thickness of 3.76 mm. The pellet thus obtained was irradiated with γ-ray (a total of 25 kGy, as a single dose) and the formulation was analyzed by HPLC, the results show the presence of up to 2.35 wt % dexamethasone RS and 0.37 wt % RS without any radiation as set forth in the Table.

A preparation of hypercompressed PLGA containing 0.23 wt % dexamethasone particles was prepared from ester capped PLGA (Resomer RG755S having an inherent viscosity of 0.5-0.7 dl/g. in 0.1 wt % in chloroform at 25° C. and a 75:25 wt. ratio of lactide to glycolide) was prepared in the same manner that the PLGA acid terminated (Purasorb 5022) formulation was prepared. This preparation was irradiated with e-beam radiation (a total of 25 kGy, as two equal doses of 12½ kGy) and the formulation was analyzed by HPLC. The results show the presence of two major dexamethasone RS materials (0.33% and 0.56%, respectively). Likewise, the same preparation was irradiated with e-beam (a total of 25 kGy, as a single dose) and the formulation was analyzed by HPLC, the results show the presence of three major Dexamethasone RS (0.1%, 0.36% and 0.57%, respectively). The same hypercompressed PLGA/Dexamethasone particles that were prepared from the same ester capped PLGA (Resomer RG755S) shows the presence of 2.16% dexamethasone RS after γ-irradiation and 0.4 wt % RS without any radiation as set forth in the Table.

The hypercompressed particles were sterilized by either γ-irradiation or e-beam, the API Dexamethasone was used as a control. The results are summarized in the Table below.

TABLE

| Irradiation | Dose (kGy) × pass | Dexamethasone | Dexamethasone/PLGA (Acid capped PLGA) | Dexamethasone/PLGA (Ester capped PLGA) |
|---|---|---|---|---|
| None | N/A | 0.23% | 0.37% | 0.4% |
| γ | 25 × 1 | 0.52% | 2.35% | 2.16% |
| e-Beam | 12½ × 2 | 0.23% (1.26RRT) | N/A | 0.33% (0.90RRT) 0.56% (1.26RRT) Σ 0.89% |
| e-Beam | 25 × 1 | 0.22% (1.26RRT) | N/A | 0.36% (0.90RRT) 0.57% (1.26RRT) 0.1% (1.30RRT) Σ 1.03% |

FDA Guidance for Industry Q3B(R2) Impurities in New Drug Products and European Medicine Agency Note for Guidance on Impurities in New Drug Products (CPMP/ICH/2738/99) state that the qualification threshold for degradation products (i.e., RS) in new drug products, "1.0% or 5 µg TDI (Total Daily Intake), whichever is lower, for a maximum daily dose: <1 mg". Since the hypercompressed microparticles are a controlled release system designed specifically for highly focal and prolonged release of drugs in very small doses, the amount of drug release daily is expected to be well within the <100 µg range (substantially lower than that of the maximum allowable dose of <1 mg daily stated in the official guidance; thus, the above data indicate that the levels of identifiable RS (and the unidentified RS) are expected to be substantially less than the 5 µg maximum tolerable TDI dose allowed. Further qualification of RS are deemed unnecessary.

For gamma sterilization, the parameters were as follows:
Specified dose: 22.5 kGy to 27.5 kGy (i.e., 25 kGy±10%)
Delivered dose: 24.2 kGy to 25.8 kGy
Exposure time: 299 minutes E-beam irradiation was performed at doses of 12.5 KGy and 25 KGy in an electron-beam accelerator at an accelerating voltage of kV, at room temperature, humidity, and without the presence of oxygen in a nitrogen atmosphere. These radiation doses were chosen because previous studies had shown that polymers irradiated at these doses exhibited a moderate (SMrad) to substantial (20 Mrad) increase in their degradation rates which would give rise to pseudo surface degradation from 20-5 to 0 Mrad multi-layer film constructs.

The invention claimed is:

1. A sterile pharmaceutical dosage form which comprises an ester capped lactide polymer, an ester capped glycolide polymer or an ester capped lactide-glycolide copolymer that is hypercompressed with an active pharmaceutical ingredient selected from the group consisting of dexamethasone, prednisone, methyl prednisolone, latanoprost, unoprostone, bimatoprost, travoprost, timolol, carteolol, betaxolol, nadolol, levobuolol, dorzolamide and acetozolamide wherein said sterile pharmaceutical dosage form has been sterilized with an electron beam.

2. A sterile pharmaceutical dosage form as defined in claim 1 where the polymer is selected from the group consisting of ester capped poly(dl-lactide), ester capped polyglycolide, ester capped poly(glycolide-co-lactide), and ester capped poly(glycolide-co-dl-lactide) or a mixture of any of the foregoing.

3. A sterile pharmaceutical dosage form as defined in claim 2 where the dosage form has been compressed by the application of 50K psi to 350K psi.

4. A sterile pharmaceutical dosage form as defined in claim 3 where the dosage form has been compressed by the application of 100 Kpsi to 300 Kpsi.

5. A sterile pharmaceutical dosage form as defined in claim 4 where the active pharmaceutical ingredient is dexamethasone.

6. A sterile pharmaceutical dosage form as defined in claim 4 where the active pharmaceutical ingredient is prednisone.

7. A sterile pharmaceutical dosage form as defined in claim 4 where the active pharmaceutical ingredient is methyl prednisolone.

8. A sterile pharmaceutical dosage form as defined in claim 4 where the active pharmaceutical ingredient is latanoprost.

9. A sterile pharmaceutical dosage form as defined in claim 4 where the active pharmaceutical ingredient is timolol.

10. A sterile pharmaceutical dosage form as defined in claim 4 where the active pharmaceutical ingredient is dorzolamide.

11. A sterile pharmaceutical dosage form as defined in claim 4 where the active pharmaceutical ingredient is acetozolamide.

12. A sterile pharmaceutical dosage form as defined in claim 4 where the active pharmaceutical ingredient is bimatoprost.

13. A sterile pharmaceutical dosage form as defined in claim 4 where the active pharmaceutical ingredient is betaxolol.

14. A sterile pharmaceutical dosage form as defined in claim 3 where the dosage form has been compressed by the application of 200 Kpsi to 300 Kpsi.

15. A method of preparing a sterile hypercompressed pharmaceutical dosage form of an ester capped lactide polymer, an ester capped glycolide polymer or an ester capped lactide-glycolide copolymer which comprises:
(a) combining an active pharmaceutical ingredient selected from the group consisting of dexamethasone, prednisone, methyl prednisolone, latanoprost, unoprostone, bimatoprost, travoprost, timolol, carteolol, betaxolol, nadolol, levobuolol, dorzolamide and acetozolamide with an ester capped lactide polymer, an ester capped glycolide polymer or an ester capped lactide-glycolide copolymer to form a powdered product;

(b) hypercompressing the powdered product of step (a) to form a hypercompressed dosage form; and (c) exposing the hypercompressed dosage form of step (b) to a sterilizing amount of an E-beam radiation source to form a sterilized product.

16. A method of preparing a sterile hypercompressed pharmaceutical dosage form according to claim 15 where the dosage form has been compressed by the application of 50K psi to 350K psi.

17. A method of preparing a sterile hypercompressed pharmaceutical dosage form according to claim 15 where the dosage form has been compressed by the application of 100 Kpsi to 300 Kpsi.

18. A method of preparing a sterile hypercompressed pharmaceutical dosage form according to claim 15 where the dosage form has been compressed by the application of 200 Kpsi to 300 Kpsi.

* * * * *